(12) United States Patent
Ochi

(10) Patent No.: US 6,811,642 B2
(45) Date of Patent: Nov. 2, 2004

(54) PRODUCTION METHOD OF ABSORBENT BODY

(75) Inventor: Kengo Ochi, Tokyo (JP)

(73) Assignee: Unicharm Petcare Corporation, Tokyo (JP)

( * ) Notice: Subject to any disclaimer, the term of this patent is extended or adjusted under 35 U.S.C. 154(b) by 361 days.

(21) Appl. No.: 10/038,322

(22) Filed: Jan. 3, 2002

(65) Prior Publication Data

US 2002/0056516 A1 May 16, 2002

Related U.S. Application Data

(62) Division of application No. 09/310,419, filed on May 12, 1999.

(30) Foreign Application Priority Data

May 12, 1998 (JP) .......................................... 10-128665

(51) Int. Cl.$^7$ ......................... B32B 31/06; B32B 31/08; D04H 1/00
(52) U.S. Cl. ...................... 156/213; 156/214; 156/285; 264/101; 264/257; 264/571
(58) Field of Search ............................. 156/62.2, 213, 156/214, 285; 264/101, 257, 571

(56) References Cited

U.S. PATENT DOCUMENTS 4,888,231 A * 12/1989 Angstadt .................... 428/213
5,226,991 A * 7/1993 Svaighert .................... 156/62.2
6,080,909 A * 6/2000 Osterdahl et al. ........... 604/368

FOREIGN PATENT DOCUMENTS

DE         1510427     * 10/1970

* cited by examiner

Primary Examiner—Sam Chuan Yao
(74) Attorney, Agent, or Firm—Darby & Darby

(57) ABSTRACT

A production method of an absorbent body is provided. The method includes the steps of: supplying a first cover sheet on an outer surface of a rotating pattern drum, said pattern drum being provided with a concavity formed in a predetermined shape on the outer surface thereof; adapting the first cover sheet to the shape of the concavity and supplying an absorbent material into the concavity to form an absorbent material layer adapted to the shape of the concavity on the first cover sheet; supplying a second cover sheet toward the outer surface of the pattern drum; and separating the first cover sheet together with the absorbent material layer from the outer surface of the pattern drum and superposing the first cover sheet together with the absorbent material layer on the second cover sheet to produce an absorbent body comprised of the first cover sheet, the second cover sheet and the absorbent material layer interposed between the first cover sheet and the second cover sheet. An absorbent body produced by this method has improved absorption properties and can be used for disposable diapers, pet sheets, sanitary napkins, and the like.

10 Claims, 9 Drawing Sheets

PRODUCTION METHOD OF ABSORBENT BODY

This is a division of 09/310,419 filed on May 12, 1999.

FIELD OF THE INVENTION

This invention relates to a production method for an absorbent article (body) used for pet sheets, disposable diapers, sanitary napkins, and the like.

BACKGROUND OF THE INVENTION

Conventional production methods for producing absorbent bodies are explained with reference to FIGS. 13 and 14.

In the conventional production method of an absorbent body shown in FIG. 13, a carrier tissue 2 is drawn from a roll 2a which is supported by an axis 1 and is forwarded continuously. A pulp supplier 3 is provided above the carrier tissue 2 which is forwarded continuously. Crushed pulps are supplied from the pulp supplier 3 to be poured on the carrier tissue 2. A supply nozzle 4 for supplying particulate SAP (super-absorbent polymers) is provided above the carrier tissue 2, and supplies the SAP on the carrier tissue 2 which is forwarded continuously.

A suction chamber 6 is provided opposite the pulp supplier 3 and the supply nozzle 4 with the carrier tissue 2 interposed. Crushed pulp and the SAP are sucked by the suction chamber 6 to form a strip of an absorbent material layer 5 comprised of a mixture of crushed pulp and SAP on the carrier tissue 2.

For a faster production, crushed pulp and SAP are continuously supplied onto the carrier tissue 2 to form a strip of an absorbent material layer 5. Thereafter, a cover tissue (not shown) is supplied onto the strip of the absorbent material layer 5 to form a laminated body, which comprises the carrier tissue 2, a cover tissue and the absorbent material layer 5 interposed between the tissues. Both sides of the laminated body are then cut by a cutter, such as a rotary cutter, and thereafter the laminated body is cut into individual absorbent bodies.

In the conventional production method of an absorbent body shown in FIG. 14, the carrier tissue 2 drawn from the roll 2a is forwarded continuously. A circular pattern drum 7 is provided above the carrier tissue 2 which is forwarded continuously. The pattern drum 7 rotates in the clockwise direction around the axis 8 at the running speed of the carrier tissue 2.

Concavities 9 are provided on the outer face of the pattern drum 7 at predetermined intervals. Mesh 9a of a predetermined screen dimension is provided at the bottom of the concavity 9. The concavity 9 is formed in a predetermined shape such as the shape of an hourglass. A pulp supplier 11 is provided above the pattern drum 7, facing the outer surface of the pattern drum 7. A supply nozzle 12 for supplying SAP is provided also facing the outer surface of the pattern drum 7.

According to the production method of the absorbent body as shown in FIG. 14, crushed pulp is supplied from the pulp supplier 11 into the concavity 9 which is provided on the outer surface of the rotating pattern drum 7. Also, SAP is supplied from the nozzle 12 into the concavity 9 in the same manner.

A suction means is provided inside of the pattern drum 7 facing the pulp supplier 11 and the supply nozzle 12 for sucking air through the openings of the mesh 9a provided at the bottom of the concavity 9. The crushed pulps and the particulate SAP are sucked onto the concavity 9, thereby forming an absorbent material layer 13 having the same shape as the concavity 9.

At the time the concavity 9 faces the carrier tissue 2 during the course of rotation of the pattern drum 7, another suction means provided below the carrier tissue 2 sucks air through the carrier tissue 2. By this suction, the absorbent material layer 13 is transferred onto the carrier tissue 2. Subsequently, a cover tissue (not shown) is laid along the carrier tissue 2 and the absorbent material layer 13, thereby forming a laminated body comprised of the carrier tissue 2, the cover tissue and the absorbent material layer 13 interposed between the tissues. Thereafter, the carrier tissue 2 and the cover tissue are cut in accordance with the shape of the absorbent material layer 13 to produce individual absorbent bodies.

In high speed production of the absorbent body, according to the conventional production method shown in FIG. 13, because the absorbent material layer 5 is formed in a strip shape on the carrier tissue 2 in a continuous process, a rectangular absorbent body is produced. However, it is almost impossible to produce an absorbent body having a desired shape, such as an hour glass shape. Therefore, in order to produce an absorbent body having a desired shape, e.g., hour glass shape, it is necessary to perform a trimming process to such laminated body in a press working process. However, this results in many additional processing steps.

In addition, in order to laminate another absorbent material layer on the absorbent material layer 5 formed by the conventional production method shown in FIG. 13, crushed pulp and SAP must be sucked by the suction means through the carrier tissue 2 and the absorbent material layer 5. However, due to the poor air permeability of the laminated layers formed from the carrier tissue 2 and the absorbent material 5, it is almost impossible to form another absorbent material layer over the laminated body by sucking additional crushed pulp or SAP by the suction means. For this reason, in the production of the absorbent body having two absorbent material layers laminated, each of the absorbent material layers must be produced separately by the method shown in FIG. 13 and each laminated thereafter. Therefore, conventional methods inevitably use many production steps to produce an absorbent body having two absorbent material layers therein.

Moreover, in order to cut an absorbent body having two laminated absorbent material layers therein, another cover tissue must to be laid over the absorbent material layer at the upper side. Consequently, at least three tissue layers are needed, making the production of the absorbent body expensive.

On the other hand, according to the conventional production method of the absorbent body shown in FIG. 14, the absorbent material layer 13 can be formed in the same shape as that of the concavity 9 formed on the outer face of the pattern drum 7.

However, in order to form the absorbent material layer 13 in the same shape as that of the concavity 9, crushed pulp and particulate SAP must be sucked into the concavity 9 by the suction force through the openings of the mesh 9a provided at the bottom of the concavity 9. In general, the opening size of the mesh 9a is 60 mesh (according to the standard of Tyler, U.S.A. the opening size of such mesh is equal to 0.246 mm).

However, because of the fineness of the SAP supplied to the concavity 9, SAP easily passes into the inside of the pattern drum 7 through the mesh 9a, thereby rendering a very poor yield ratio of SAP. Due to the passage of SAP through the mesh 9a, which results in a poor yield ratio of SAP, it is very difficult to increase the content of SAP in the absorbent layer 13. Therefore, it is extremely difficult to produce an absorbent layer containing 20% SAP or more by weight.

Further, in order to accelerate the liquid absorption speed of the absorbent material layer, the particle size of SAP present in the absorbent material layer must be very small. However, the mesh 9a having the opening size of 60 mesh can hardly prevent such fine SAP from passing through into the pattern drum 7. Therefore, it is almost impossible for the mesh 9a to hold SAP having a small particle size, such as 100 mesh or less (which passes through a mesh having an opening size of 0.147 mm) at the concavity 9.

In addition, according to the conventional production method shown in FIG. 14, the absorbent material layer 13 must be sucked through the carrier tissue 2 by the suction means provided below the carrier tissue 2 at the time the concavity 9 faces the carrier tissue 2. However, in order to suck the absorbent material layer formed in the concavity 9 through the carrier tissue 2, a very strong suction force is needed. Consequently, the suction means inevitably becomes large, making the production cost very high.

Furthermore, according to the conventional production method as shown in FIG. 14, it is very difficult to produce an absorbent body having two absorbent material layers laminated to each other. Sucking another absorbent material layer onto the absorbent body, by sucking through the carrier tissue 2 and the absorbent material layer 13 using a suction means, is almost impossible because of the poor air permeability of the layers. Therefore, in order to produce an absorbent body having two absorbent material layers laminated therein, each of the absorbent material layers must be produced separately and thereafter laminated to each other, such as the production method shown in FIG. 13. Consequently, the number of steps for producing the absorbent body having two absorbent material layers laminated to each other is inevitably increased.

Also, similar to the production method shown in FIG. 13, in order to cut the absorbent body having two laminated absorbent material layers therein, another cover tissue must be laid over the absorbent material layer at the upper side. As a result, at least three tissue layers become necessary, making the production of the absorbent body expensive.

SUMMARY OF THE INVENTION

It is an object of the present invention to provide a production method of an absorbent body which overcomes the aforementioned problems by transferring the absorbent material layer formed in the concavity of the pattern drum onto the cover sheet without using a large scaled suction means of the conventional technology.

It is a further object of the present invention to improve the yield ratio of SAP present in the absorbent material layer, thereby achieving an absorbent body containing an increased amount of SAP or fine SAP.

It is a further object of the present invention to provide a production method of an absorbent body that can laminate a plurality of absorbent material layers without using a cover sheet between the laminated absorbent material layers.

It is a further object of the present invention to produce an absorbent body by laminating a plurality of absorbent material layers wherein each layer can have a different shape, different SAP contents, or different particle sizes for SAP.

To achieve these objects, the production method of the present invention comprises the steps of:

(1) supplying a first cover sheet on an outer surface of a rotating pattern drum, said pattern drum provided with a concavity formed in a predetermined shape on the outer surface thereof;

(2) adapting the first cover sheet to the shape of the concavity and supplying an absorbent material into the concavity to form an absorbent material layer adapted to the shape of the concavity on the first cover sheet;

(3) supplying a second cover sheet toward the outer surface of the pattern drum; and (4) separating the first cover sheet together with the absorbent material layer from the outer surface of the pattern drum and superposing the first cover sheet together with the absorbent material layer on the second cover sheet to produce an absorbent body comprised of the first cover sheet, the second cover sheet and the absorbent material layer interposed between the first cover sheet and the second cover sheet.

In this production method, it is also possible that another absorbent material layer is formed on the second cover sheet, and the absorbent material layer formed on the first cover sheet is superposed on the absorbent material layer formed on the second cover sheet, between the first cover sheet and the second cover sheet.

Another production method of the absorbent body according to the present invention comprises the steps of:

(1) supplying a first cover sheet on an outer surface of a first pattern drum rotating, said first pattern drum being provided with a first concavity formed in a predetermined shape on the outer surface thereof;

(2) adapting the first cover sheet to the shape of the first concavity and supplying an absorbent material into the first concavity to form a first absorbent material layer adapted to the shape of the first concavity on the first cover sheet;

(3) supplying a second cover sheet on the outer surface of a second pattern drum rotating, said second pattern drum being provided with a second concavity formed in a predetermined shape on the outer surface thereof;

(4) adapting the second cover sheet to the shape of the second concavity and supplying an absorbent material into the second concavity to form a second absorbent material layer adapted to the shape of the second concavity on the second cover sheet; and (5) separating the first cover sheet together with the first absorbent material layer from the outer surface of the first pattern drum and separating the second cover sheet together with the second absorbent material layer from the outer surface of the second pattern drum and superposing the first cover sheet together with the first absorbent material layer on the second cover sheet together with the second absorbent material layer to produce an absorbent body comprised of the first cover sheet, the second cover sheet and the first and second absorbent material layers interposed between the first cover sheet and the second cover sheet.

DETAILED DESCRIPTION OF THE INVENTION

Figure 1:
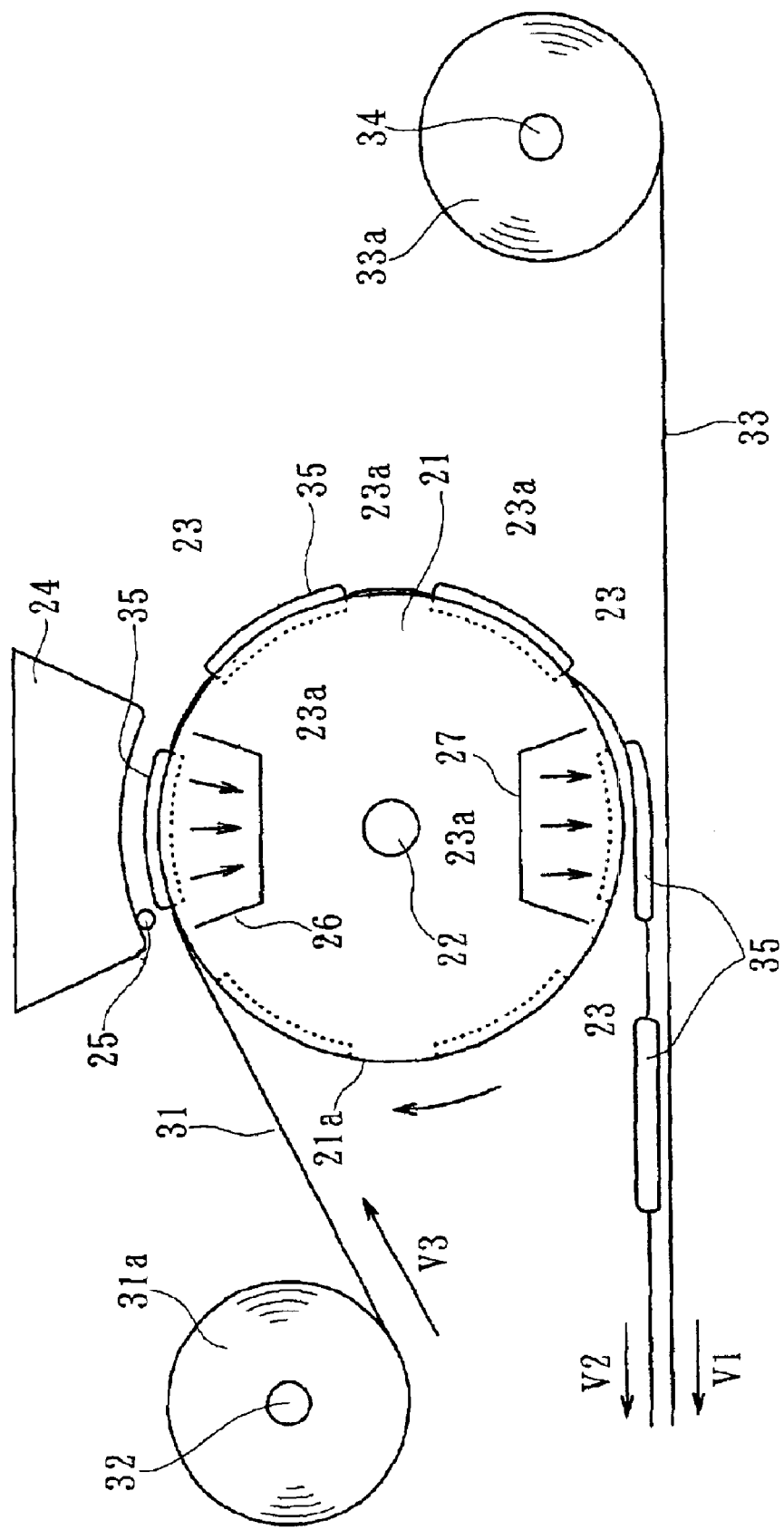
FIG. 1 is a schematic diagram of the production method of the absorbent body showing one embodiment of the present invention.

FIG. 1 shows one embodiment of the present invention, and is provided by way of example.

According to the production method of the absorbent body shown in FIG. 1, an absorbent body comprising a single absorbent material layer held between two cover sheets is produced.

Figure 4:
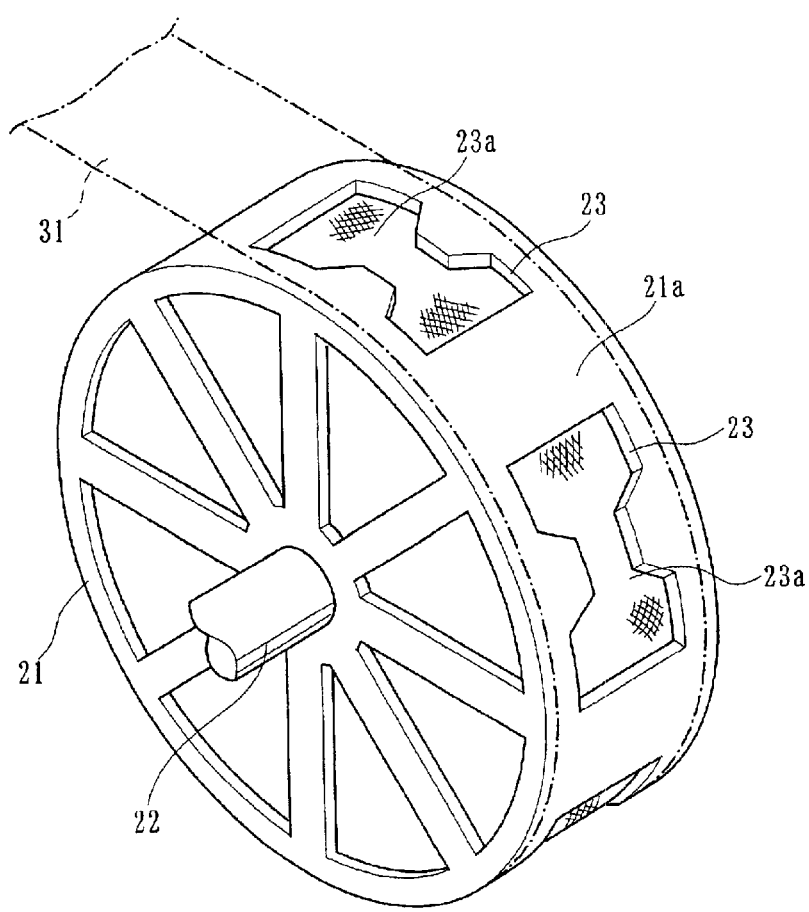
FIG. 4 is a partial perspective view of the outer surface of a pattern drum of the present invention.

A pattern drum 21 is continuously rotated around an axis 22 in the clockwise direction at a certain rotating speed. As shown in FIG. 4, concavities 23 are formed on an outer surface 21a of the pattern drum 21 by predetermined intervals. The shape of the concavity 23 is like an hourglass. Mesh 23a is formed at the bottom of the concavity 23 having a screen of 60 mesh (having an opening of 0.246 mm) according to the standard of Tyler, U.S.A.

As shown in FIG. 1, a pulp supplier 24 for supplying absorbent fibers such as crushed pulp and a supply nozzle 25 for supplying particulate SAP (super-absorbent polymers) is provided above the pattern drum 21, facing the outer surface 21a thereof. The relative position between the supply nozzle 25 and the pulp supplier 24 can be determined appropriately depending on the desired position of supplying the SAP to the crushed pulp.

The SAP can be made of polyacrylic acid, sodium polyacrylate, polyacrylamide, polyacrylonitrile, polyvinyl alcohol, an additional polymer of maleic anhydride, a polyether, a condensed polymer, a polysaccharide such as starch or cellulose, a protein such as collagen, or the like. Examples of SAPs include: a cross-linked compound of sodium polyacrylate, a graft copolymer of starch having sodium polyacrylate or a graft copolymer of cellulose having polyacrylonitrile chains.

A suction chamber 26 is provided inside the pattern drum 21, facing the pulp supplier 24 and the supply nozzle 25. Also, a pressure chamber 27 is provided inside the pattern drum 21, facing the inside face of concavity 23 when it is moved to the bottom of the pattern drum 21. The suction chamber 26 sucks the air through the mesh 23a of concavity 23 when concavity 23 is moved to the top position. The pressure chamber 27 forces the air through the mesh 23a of the concavity 23 when the concavity 23 is moved to the bottom position.

A cover tissue 31 which becomes a first cover sheet of the absorbent body is drawn from a roll 31a rotating around an axis 32, wound around the outer surface 21a of the pattern drum 21 and thereafter forwarded to the left as shown in FIG. 1. A carrier tissue 33 which becomes a second cover sheet of the absorbent body is drawn from a roll 33a rotating around an axis 34 and thereafter forwarded continuously (to the left) at a certain speed as shown in FIG. 1.

The carrier tissue 33 is forwarded at the speed of V1 by the force of a conveyor (not shown), being proceeded by the rotation of conveyor rolls provided at the left of the pattern drum 21. The cover tissue 31 is forwarded to the left at the speed of V2, after proceeding around the outer surface 21a of the pattern drum 21. The speed V1 and V2 are set equal to each other.

Figure 5:
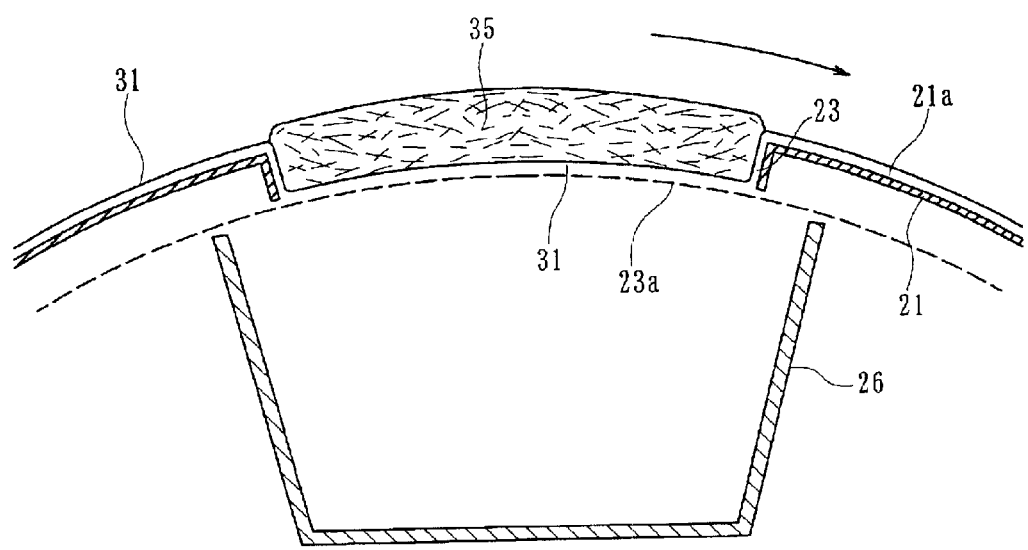
FIG. 5 is a partial sectional view of a pattern drum showing the state of an absorbent material layer formed on the outer surface thereof.

As shown in FIG. 5, the cover tissue 31, drawn from a roll 31a is laid along (or adapted to) the inner surface of the concavity 23 to form a concave shape and thereafter moves together with the outer surface 21a of the pattern drum 21 in a clockwise direction. The rotating speed of the outer surface 21a of the pattern drum 21 is set almost equal to the forwarding speed V1 of the carrier tissue 33. However, since the cover tissue 31 is laid along the inner surface of the concavity 23, the speed V3 of drawing out the cover tissue 31 from the roll 31a is set slightly faster than the speed V1 or V2.

The production method of the absorbent body shown in FIG. 1 is explained in detail.

The pattern drum 21 is rotated in the clockwise direction at a certain speed, and the cover tissue 31 which becomes the first cover sheet of the absorbent body is supplied to the outer surface 21a of the pattern drum 21. When the concavity 23 is moved to the top of the pattern drum 21 (i.e., above the suction chamber 26), the sucking force of the suction chamber 26 is applied to the cover tissue 31 through the mesh 23a, to lay the cover tissue 31 along the surface of the concavity 23 and thereby deform the cover tissue in a concave shape.

The crushed pulp is supplied into the concavity 23 by the pulp supplier 24 and the particulate SAP is supplied into the concavity 23 from the supply nozzle 25 at the same time. The crushed pulp and the SAP are sucked into the concavity 23 through the mesh 23a and the cover tissue 31. Consequently, the cover tissue 31 is laid along the inner surface of the mesh 23a in the concavity 23, to thereby form the absorbent material layer 35, comprised of a mixture of crushed pulp and SAP, on the cover tissue 31, as shown in FIG. 5. The shape of this absorbent material layer 35 is the same as the shape of the concavity 23 opening upward. Thus, in the case of using the pattern drum 21 shown in FIG. 4, the shape of this absorbent material layer 35 can be formed in an hourglass shape. By setting up the relative position of the supply nozzle 25 and the pulp supplier 24 as shown in FIG. 1, the content of SAP in the absorbent material layer 35 can be arranged such that more of the SAP exists at a position proximate to the cover tissue 31.

In another embodiment, the carrier tissue 33 is supplied from the roll 33a and is forwarded underneath the pattern drum 21. When the concavity 23 is moved to the bottom of the pattern drum 21 and faces the carrier tissue 33, the absorbent material layer 35 and the cover tissue 31 are separated from the concavity 23 by the pressure chamber 27. Thus, the absorbent material layer 35 is transferred to the carrier tissue 33 together with the cover tissue 31. In this process, an air pressure force is applied to the cover tissue 31 by the pressure chamber 27 to push out the absorbent material layer 35 and the cover tissue 31 from the concavity 23 of the pattern drum 21. Incidentally, although it is preferable to push out the absorbent material layer 35 and the cover tissue 31 by the pressure chamber 27, the absorbent material layer 35 may be separated from the concavity 23 by applying some other force to the cover tissue 31 in the direction of the carrier tissue 33.

As a result, a laminated body comprising the carrier tissue 33 and the cover tissue 31 having the absorbent material layers 35 at predetermined intervals between them is produced. By cutting the laminated body into predetermined dimensions at positions between adjacent absorbent material layers 35 using a cutter, e.g., a rotary cutter, individual absorbent bodies are produced.

In the production of a laminated body (absorbent body), a hot melt type adhesive can be applied between the absorbent material layer 35 and the cover tissue 31 and/or between the absorbent material layer 35 and the carrier tissue 33. Also, the cover tissue 31 and the carrier tissue 33 can be adhered with each other at the peripheral of the absorbent material layer 35.

Since the cover tissue 31 is laid on the mesh 23a at the bottom of the concavity 23 of the pattern drum 21 and crushed pulp and particulate SAP are supplied thereon, the particulate SAP does not pass into the inside of pattern drum 21 through the screen of mesh 23a. This improves the yield ratio of SAP. Also, since the SAP content in the absorbent material layer 35 can be increased, the water retention property of the absorbent material layer 35 can be improved. Further, since the SAP is prevented from passing through the screen of mesh 23a, the SAP content in the absorbent material layer 35 can be freely determined and the scattering of the SAP content among the absorbent bodies can be decreased. Moreover, since the SAP, having a small particle size of 100 mesh or smaller (which passes through a screen having an opening of 0.147 mm) or 200 mesh or smaller (which passes through a screen having an opening of 0.074 mm), can be introduced into the absorbent material layer 35, the liquid absorption speed of the absorbent material layer 35 can be accelerated.

According to the production method of the present invention, SAP, having a particle size in the range of 60 mesh to 200 mesh can be introduced into the absorbent material layer 35 in the range of 20% to 90% by weight. It is even possible to mix SAP having a smaller particle size than 200 mesh into the absorbent material layer 35.

In the production method shown in FIG. 1, it is possible to supply only crushed pulp without supplying SAP to form the absorbent material layer 35. Even in this embodiment, since the absorbent material layer 35 can be separated from the concavity 23 together with the cover tissue 31 laid along the concavity 23, the absorbent material layer 35 can be easily removed from the concavity 23.

Figure 2:
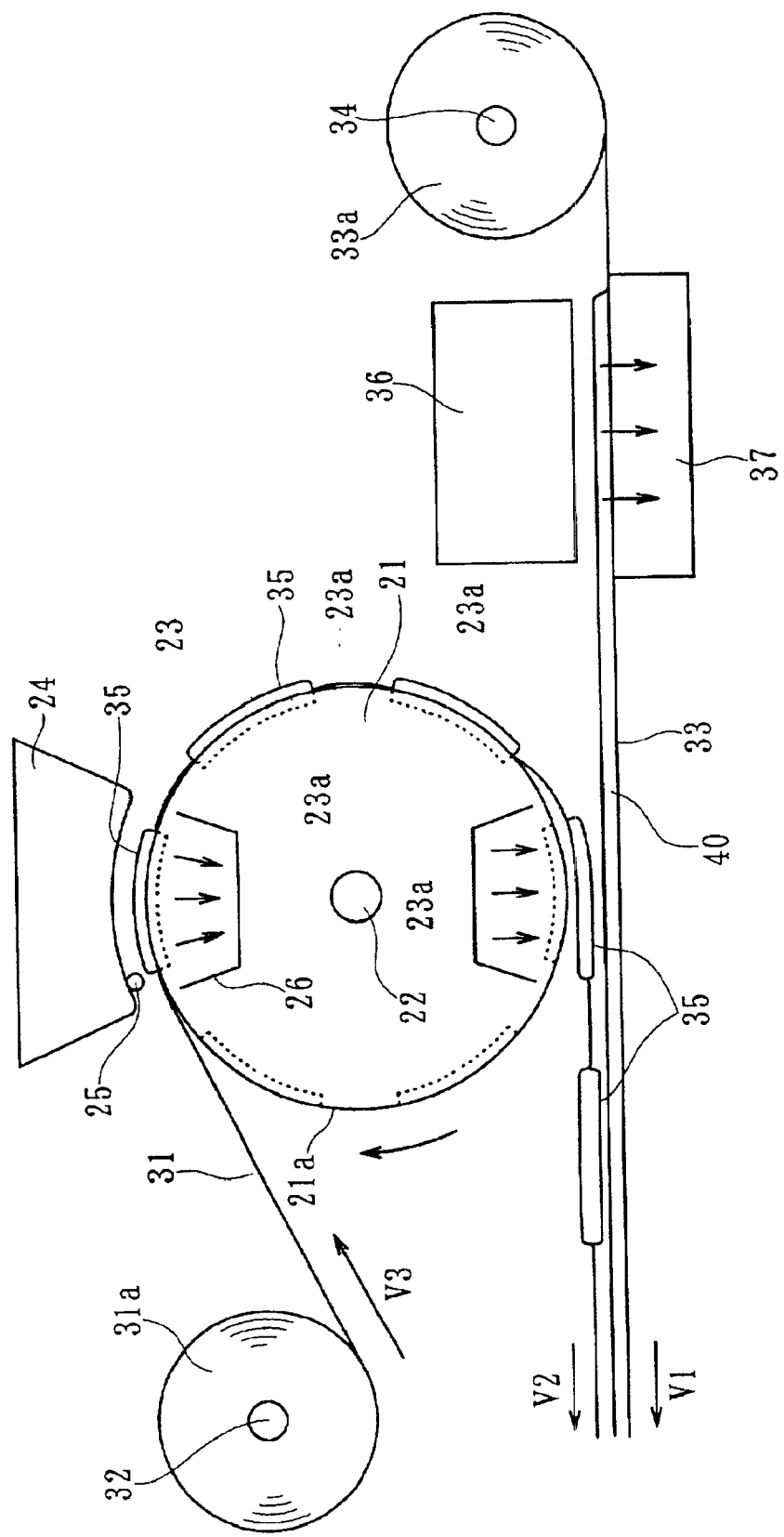
FIG. 2 is a schematic diagram of a production method of an absorbent body showing another embodiment of the present invention.

FIG. 2 shows another production method of the absorbent body of the present invention.

In the production method shown in FIG. 2, another pulp supplier 36 is provided above the carrier tissue 33 drawn from the roll 33a to become the second cover sheet. Underneath the pulp supplier 36, another suction chamber 37 is provided which faces the pulp supplier 36 with the carrier tissue 33 interposed between them. It is noted that hereinafter the members and means having the same structure as in FIG. 1 are indicated by using the same reference numbers. Therefore, the pattern drum 21, the cover tissue 31 (which becomes the first cover sheet of the absorbent body by being supplied to the outer surface 21a of the pattern drum 21), the pulp supplier 24 and the supply nozzle 25, all shown in FIG. 2, are the same as those shown in FIG. 1.

According to the production method shown in FIG. 2, the carrier tissue 33, which becomes the second cover sheet of the absorbent body, is drawn from the roll 33a and forwarded continuously at a certain speed V1. Crushed pulp is supplied on the carrier tissue 33 from the pulp supplier 36. The crushed pulp is sucked onto the carrier tissue 33 by the air suction force generated by the suction chamber 37 to form another absorbent material layer 40 in a continuous strip on the carrier tissue 33.

Similar to the production method shown in FIG. 1, when absorbent material layer 40 and the carrier tissue 33 are underneath the pattern drum 21, the absorbent material layer 35 (formed at the concavity 23 of the pattern drum 21) and the cover tissue 31 are separated from the concavity 23 and laid on the absorbent material layer 40. By this process, a double layered absorbent material can be formed between the carrier tissue 33 and the cover tissue 31. Consequently, a laminated body, comprised of the carrier tissue 33 and cover tissue 31 with the absorbent material having a double layered structure interposed between them, can be produced. By cutting this laminated body by a cutter, e.g., a rotary cutter in a predetermined dimension, the individual absorbent bodies are produced.

The absorbent material layer 35 and the cover tissue 31 can be adhered to each other by using a hot melt type adhesive. Also, the absorbent material layer 40 and the carrier tissue 33 can be adhered to each other by using the same type of adhesive. Further, the cover tissue 31 and the carrier tissue 33 can be adhered to each other at the periphery of the double layered absorbent material formed from the absorbent material layer 35 and the absorbent material layer 40.

According to the production method shown in FIG. 2, since it is not necessary to have tissue between the absorbent material layer 40 and the absorbent material layer 35, an absorbent body having an absorbent material layer formed of a double layer structure can be produced at low cost.

According to the production method shown in FIG. 2, SAP can be introduced into the absorbent material layer 35 without introducing SAP into the absorbent material layer 40. Alternatively, the absorbent material layer 40 also can be formed from a mixture of crushed pulp and SAP by installing another supply nozzle of SAP with the pulp supplier 36. In this embodiment, when forming the absorbent material layer 35 and the absorbent material layer 40 from a mixture of crushed pulp and SAP, it is possible to make the contents and particle sizes of the SAP different in the absorbent material layer 35 and the absorbent material layer 40.

Alternatively, it is also possible to form the absorbent material layer 35 from crushed pulp alone while the absorbent material layer 40 is formed from the mixture of crushed pulp and SAP.

Figure 3:
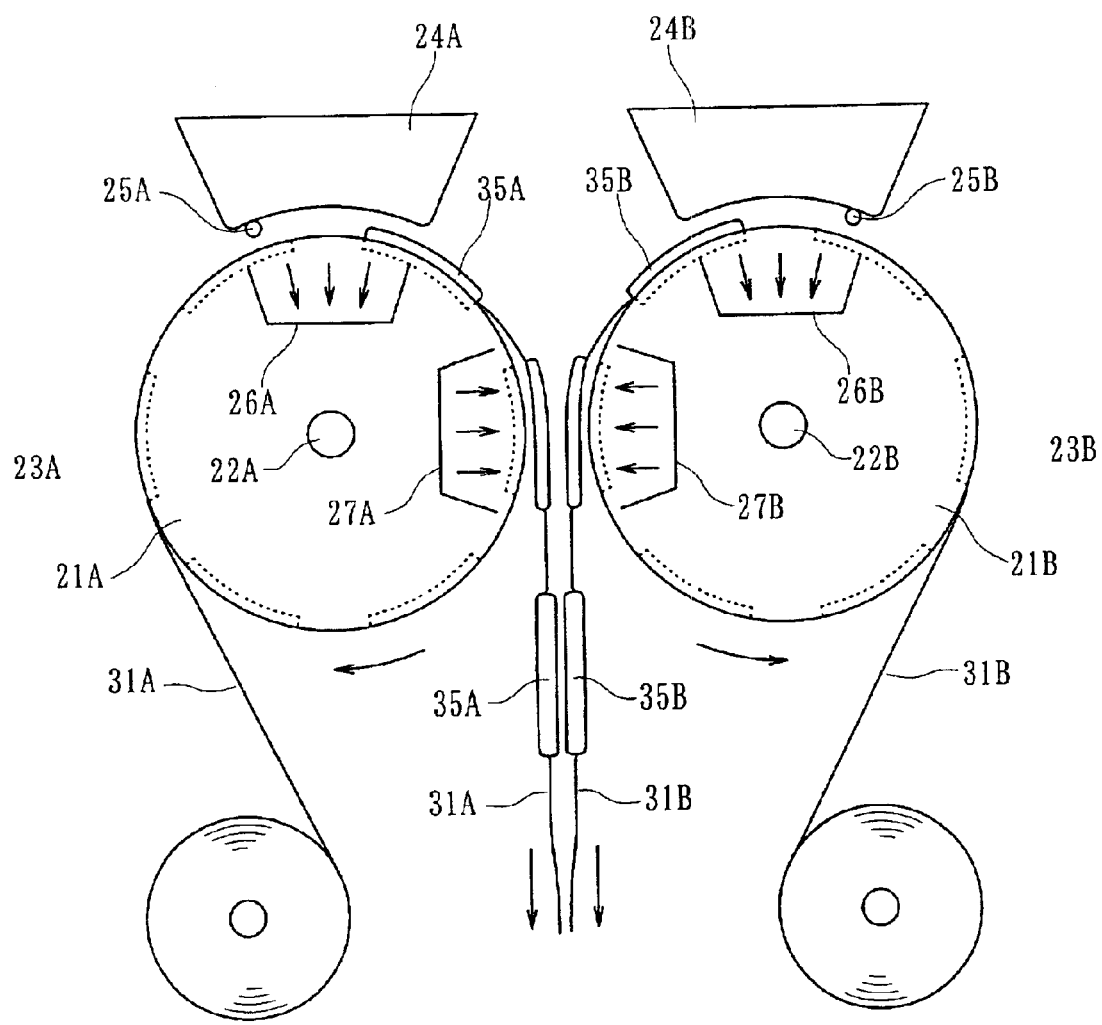
FIG. 3 is a schematic diagram of a production method of an absorbent body showing another embodiment of the present invention.

FIG. 3 shows another production method of the absorbent body of the present invention.

In this embodiment of the production method, a first pattern drum 21A and a second pattern drum 21B, which have the same structure as the pattern drum 21 shown in FIGS. 1, 2, 4 and 5, are provided in parallel. The first pattern drum 21A continuously rotates in the clockwise direction, and the second pattern drum 21B continuously rotates in the counterclockwise direction, both at the same speed. Also, similar to the pattern drum 21, concavities 23A and concavities 23B, the bottoms of which are formed as mesh having a screen of 60 mesh, are provided on the outer surface of pattern drum 21A and on the outer surface of pattern drum 21B, respectively. The concavities 23A and 23B may be formed having the same or different shapes.

A pulp supplier 24A and a supply nozzle 25A for SAP are provided above the pattern drum 21A. A suction chamber 26A is provided inside the pattern drum 21A. Similarly, a pulp supplier 24B and a supply nozzle 25B for SAP are provided above the pattern drum 21B. A suction chamber 26B is provided inside the pattern drum 21B.

A pressure chamber 27A and a pressure chamber 27B are provided inside the pattern drum 21A and the pattern drum 21B, respectively. The pressure chambers 27A and 27B are facing each other at the position where the outer surfaces of the pattern drum 21A and the pattern drum 21B are facing each other with the cover tissues 31A and 31B interposed between them.

According to the production method of the absorbent body as shown in FIG. 3, the cover tissue 31A is supplied to the outer surface of the first pattern drum 21A and laid along the inside of the concavity 23A. Crushed pulp and SAP are supplied from the pulp supplier 24A and supply nozzle 25A, respectively, into the concavity 23A. This forms a first absorbent layer 35A comprising a mixture of crushed pulp and SAP on the cover tissue 31A, the shape of which is the same as that of the concavity 23A. Also, the cover tissue 31B is supplied to the outer surface of the second pattern drum 21B. This cover tissue 31B is laid along the inside of the concavity 23B of the second pattern drum 21B. Crushed pulp and SAP are supplied from the pulp supplier 24B and the supply nozzle 25B, respectively, to form a second absorbent material layer 35B, the shape of which is the same as that of the concavity 23B.

At a position where the outer surfaces of the pattern drums 21A and 21B face each other, with the cover tissue 31A and 31B interposed between them. The cover tissue 31A is separated from the concavity 23A together with the absorbent material layer 35A by the pressure chamber 27A. The cover tissue 31B is separated from the concavity 23B together with the absorbent material layer 35B by the pressure chamber 27B. Thereafter, the absorbent material layer 35A and the absorbent material layer 35B are superposed onto each other to have a double layer structure, between the cover tissue 31A and the cover tissue 31B, thereby forming a laminated body.

Subsequently, such laminated body is cut into pieces in a predetermined dimension to produce the individual absorbent bodies.

The absorbent material layer 35A and the cover tissue 31A can be adhered each other by using a hot melt type adhesive. Also, the absorbent material layer 35B and the cover tissue 31B can be adhered to each other by using the same type of adhesive. It is also possible to adhere the cover tissue 31A and 31B to each other at the periphery of the absorbent material to form a double layer structure of the absorbent material layers 35A and 35B.

In this production method, since no tissue is necessary between the absorbent material layer 35A and the absorbent material layer 35B, an absorbent body having double layered absorbent material structure is produced at low cost.

If desired, SAP can be introduced into either one of the absorbent material layers 35A or 35B. Also, it is possible to make the contents and particle sizes of the SAP different in each absorbent material layer 35A and 35B.

Instead of laminating (or superposing) the absorbent material layers 35A and 35B, they can be combined such that they are adjacent to each other in a horizontal plane to form a single-flat layered structure between the cover tissues 31A and 31B as described below (with reference to FIGS. 10–12).

The following disclosure describes the structure of the absorbent bodies produced according to the production methods explained above.

Figure 6A:
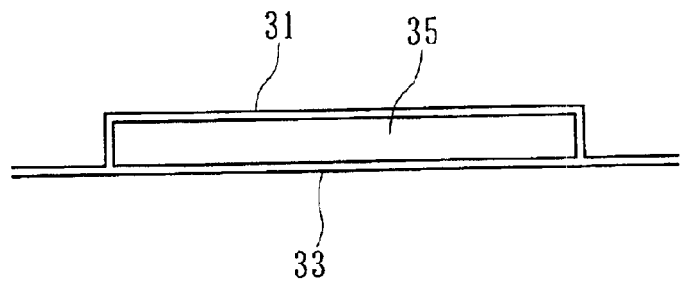
FIG. 6(A) is a sectional view of an absorbent body produced according to a production method of the present invention.

FIG. 6(A) shows an absorbent body produced according to a production method shown in FIG. 1. This absorbent body is comprised of the carrier tissue 33 and the cover tissue 31 with the absorbent material layer 35 interposed between them. The absorbent material layer 35 is formed from crushed pulp or a mixture of crushed pulp and SAP.

Figure 6B:
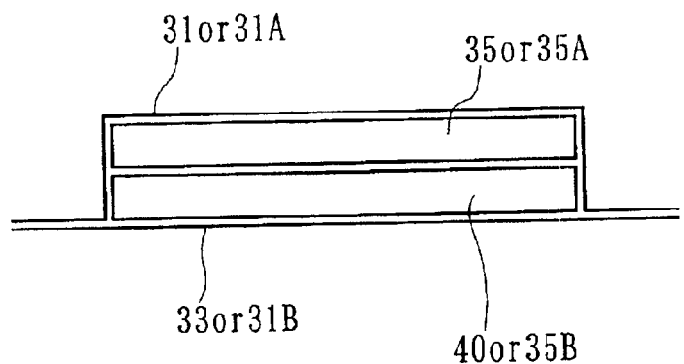
FIG. 6(B) is a sectional view of an absorbent body produced according to a production method of the present invention.

FIG. 6(B) shows an absorbent body produced according to a production method shown in FIGS. 2 or 3.

In the production method shown in FIG. 2, the absorbent material layer 40 and the absorbent material layer 35 formed in the concavity 23 of the pattern drum 21 are laminated to each other, which laminated layers are held between the carrier tissue 33 and the cover tissue 31.

Figure 7:
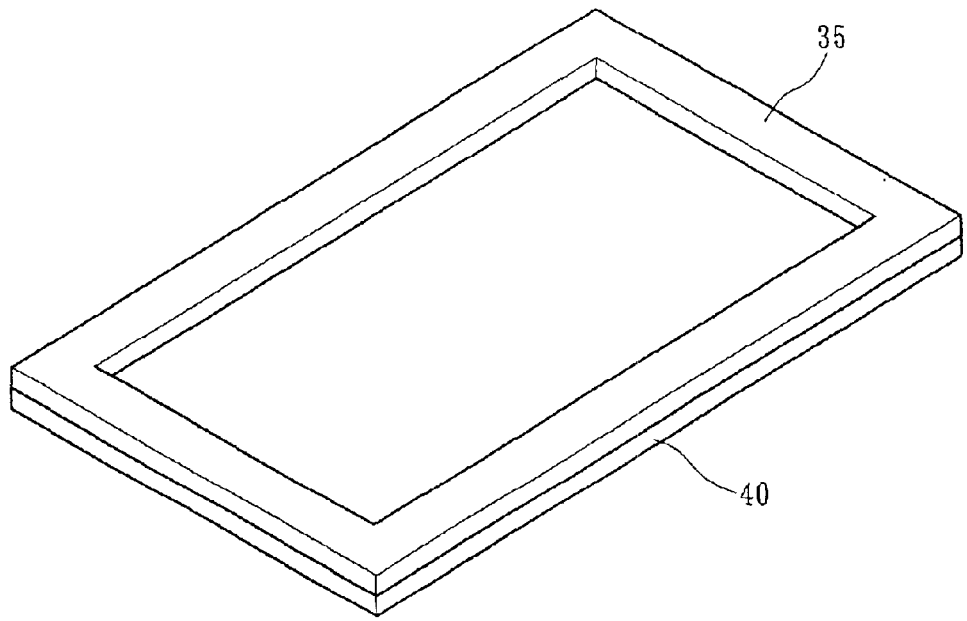
FIG. 7 is a perspective view of an absorbent material layer produced according to a production method of the present invention as shown in FIG. 2.

One example of the shape of the laminated layers, according to a production method shown in FIG. 2, is illustrated in FIG. 7. The absorbent material layer 35 in a rectangular framework shape is laminated on the absorbent material layer 40. This absorbent material layer 35 in a rectangular framework shape can be formed by forming the concavity 23 of the pattern drum 21 in a rectangular framework shape.

The absorbent body having the laminated layers shown in FIG. 7 can be used as an absorption sheet for pet excrement, or the like, which can be produced by providing a liquid, non-permeable backing sheet at the bottom of the absorbent body and a liquid permeable top sheet on the top of the same. The absorbent material layer 40 is formed of crushed pulp alone or a mixture of crushed pulp and SAP, and the absorbent material layer 35, having a rectangular shape, is formed of a mixture of crushed pulp and SAP. In this embodiment, it is desirable that the absorbent material layer 35 contains more and/or finer SAP than the absorbent material layer 40. The SAP contained in the absorbent material layer 35 preferably has a particle size smaller than 60 mesh, more preferably smaller than 100 mesh. The SAP content in the absorbent material layer 35 is 20% by weight or more, preferably 30% by weight or more, and more preferably, in the range of 50% to 90% by weight. In such structure, the absorption sheet can prevent urine from leaking out of the absorbent material layer 35 having a rectangular framework shape that absorbs the urine excreted on the absorbent material layer 40 very quickly.

Although one of the advantages of the production method shown in FIG. 2 is that no tissue is necessary between the absorbent material layer 40 and the absorbent material layer 35, it is preferable that the excrement absorption sheet for pets has an area surrounded by the absorbent material layer 35 which is colored. Therefore, in the production method shown in FIG. 2, a colored tissue 51 may be supplied on the absorbent material layer 40 such that the colored tissue 51 is placed between the absorbent material layer 40 and the absorbent material layer 35 as shown in FIG. 6(D) (if the absorbent body is used for the excrement absorption sheet for pets). In this embodiment, the colored tissue 51 at the area surrounded by the framework shaped absorbent material layer 35 can be seen from outside through the cover tissue 31 and the top sheet.

The structure of the absorbent body produced according to a production method shown in FIG. 3 is such that the absorbent material layer 35B formed at the concavity 23B is placed on the cover tissue 31B. The absorbent material layer 35A formed at the concavity 23A is laminated on the absorbent material layer 35B and the cover tissue 31A covers the top face thereof, as shown in FIG. 6(B). In this production method shown in FIG. 3, both the absorbent material layers 35A and 35B can be formed in any shape desired.

Figure 8:
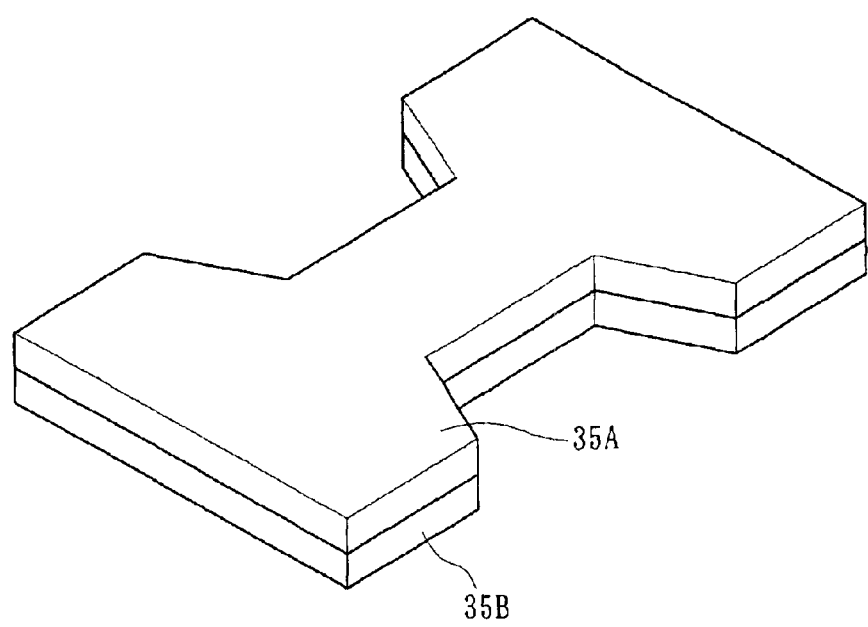
FIG. 8 is a perspective view of an absorbent material layer produced according to a production method of the present invention as shown in FIG. 3.
Figure 9:
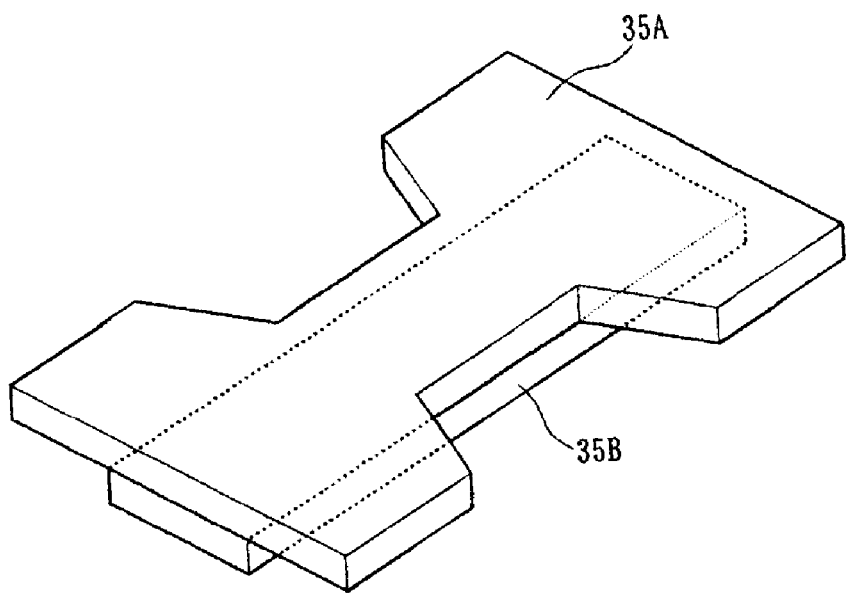
FIG. 9 is a perspective view of an absorbent material layer produced according to a production method of the present invention as shown in FIG. 3.

FIGS. 8 and 9 each show an example of the shape formed by the absorbent material layer 35B and the absorbent material layer 35A in the absorbent body produced according to the production method as shown in FIG. 3.

In FIG. 8, the absorbent material layers 35A and 35B are both formed in an hourglass shape having the same dimensions. This combination of absorbent material layers can be made by forming the concavity 23A of the first pattern drum 21A and the concavity 23B of the second pattern drum 21B in the same hourglass shape and size.

In FIG. 9, the absorbent material layer 35A at the upper side is in an hourglass shape and the absorbent material layer 35B at the lower side is in a rectangular shape. The absorbent material layer 35B at the lower side is attached to the absorbent material layer 35A at the upper side only at the central portion in a transverse direction.

The absorbent bodies having such layers 35A and 35B as shown in FIGS. 8 and 9 can be used for a disposable diaper, sanitary napkin, urine absorption pad, or the like, which can be produced by providing a liquid non-permeable backing sheet at the bottom of the absorbent body, and a liquid permeable top sheet at the top thereof.

In those absorbent bodies shown in FIGS. 8 and 9, the absorbent material layer 35A at the upper side is comprised of crushed pulp alone or a mixture of crushed pulp and SAP. The absorbent material layer 35B at the lower side is comprised of a mixture of crushed pulp and SAP. In this embodiment, it is desirable for the absorbent material layer 35B at the lower side to contain more and/or finer SAP than the absorbent material layer 35A at the upper side. The SAP contained in the absorbent material layer 35B preferably has a particle size smaller than 60 mesh, more preferably smaller than 100 mesh. The SAP content in the absorbent material layer 35B is 20% by weight or more, preferably 30% by weight or more, and more preferably, in the range of 50% to 90% by weight. In such structure, the excrement or secretion liquid introduced to the absorbent material layer 35A at the upper side is moved toward the absorbent material layer 35B at the lower side due to the strong absorption ability of the more and/or finer SAP contained in the absorbent material layer 35B, before the excrement or secretion liquid spreads over the absorbent material layer 35A at the upper side. Therefore, the excrement or secretion liquid cannot flow back to the top sheet. In the absorbent body having such a structure as shown in FIG. 9, the excrement or secretion liquid introduced to the central portion of the absorbent material layer 35A at the upper side is strongly absorbed by the more and/or finer SAP contained in the absorbent layer 35B at the lower side, and thus prevents the excrement or secretion liquid not only from flowing back to the top sheet but also from leaking to the side of the absorbent material layer 35A.

Figure 6C:
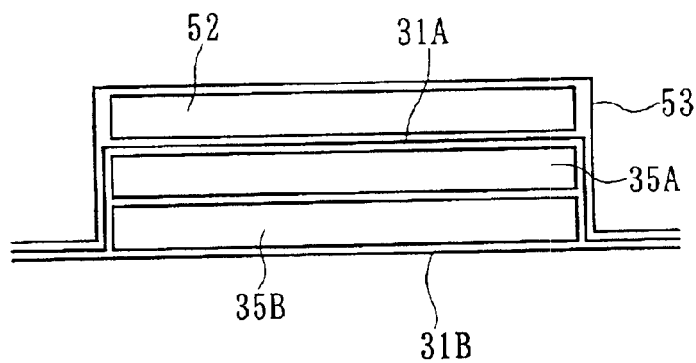
FIG. 6(C) is a sectional view of the absorbent body produced according to a production method of the present invention.
Figure 6D:
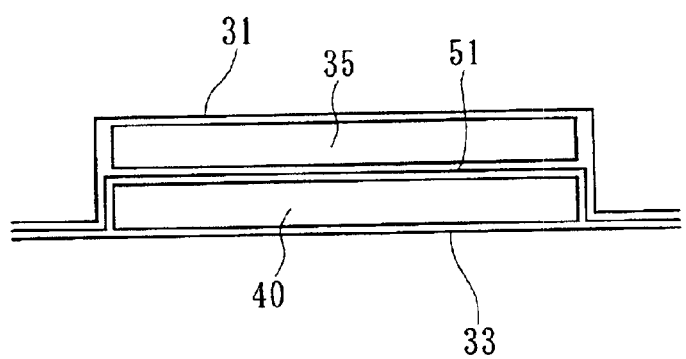
FIG. 6(D) is a sectional view of the absorbent body produced according to a production method of the present invention.

In another embodiment, modifying the production method shown in FIG. 3 produces an absorbent body having a three layered absorbent material as shown in FIG. 6(C). That is, by providing and laminating another absorbent material layer 52 formed on another cover tissue 53 onto the laminated body produced by the production method shown in FIG. 3, an absorbent body having a three layered absorbent material is produced.

Figure 10:
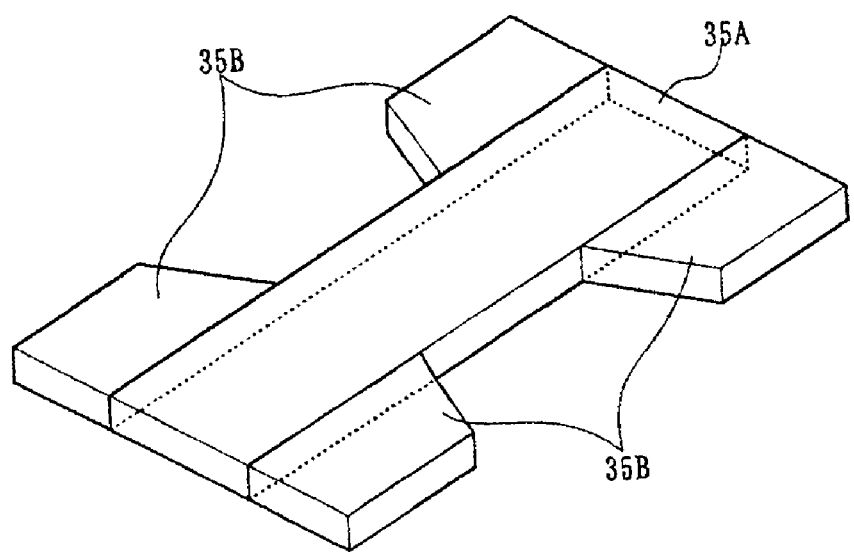
FIG. 10 is a perspective view of an absorbent material layer produced according to a production method of the present invention as shown in FIG. 3.
Figure 11:
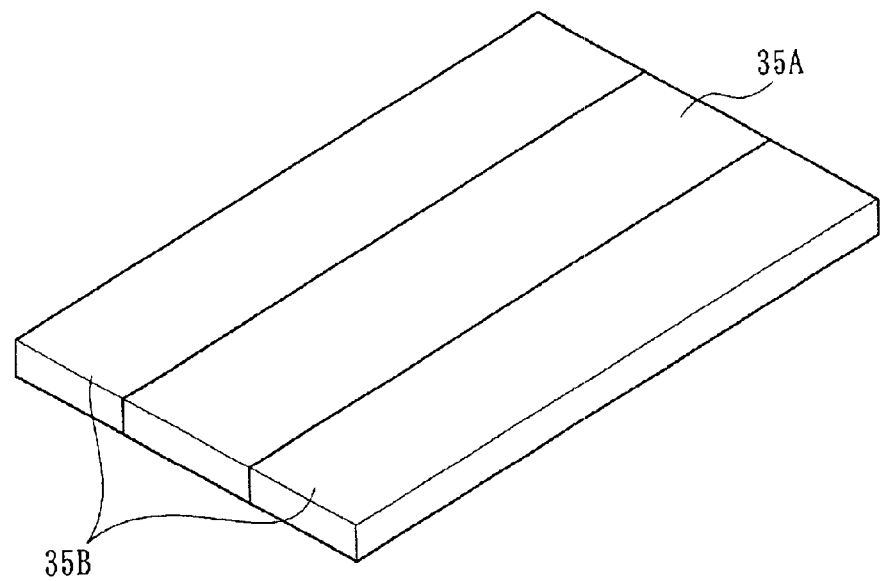
FIG. 11 is a perspective view of an absorbent material layer produced according to a production method of the present invention as shown in FIG. 3.
Figure 12:
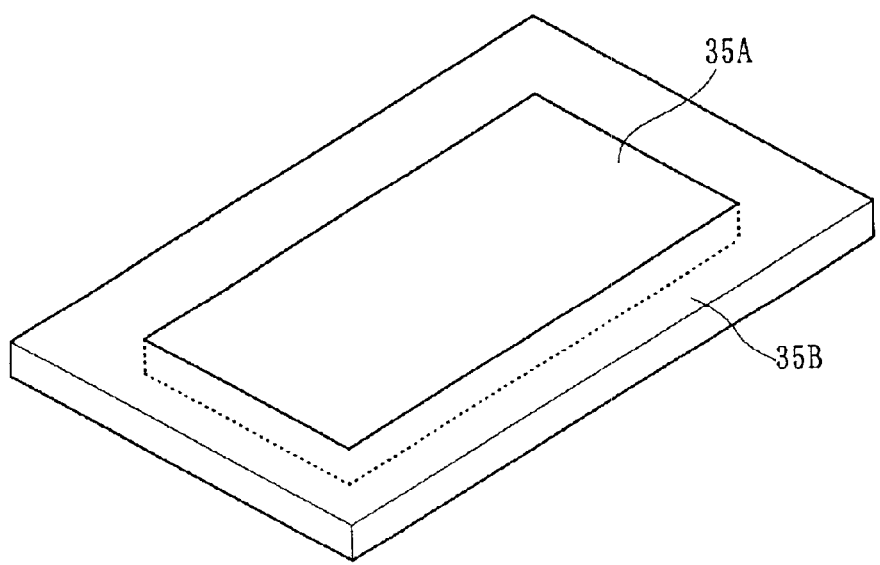
FIG. 12 is a perspective view of an absorbent material layer produced according to a production method of the present invention as shown in FIG. 3.
Figure 13:
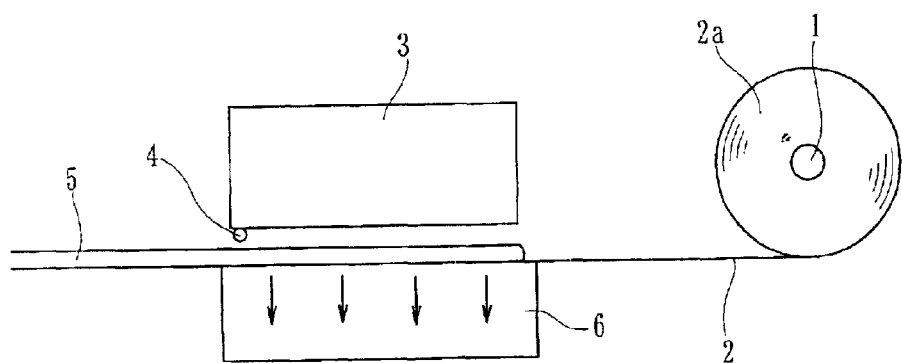
FIG. 13 is a schematic diagram showing the conventional production method of the absorbent body.
Figure 14:
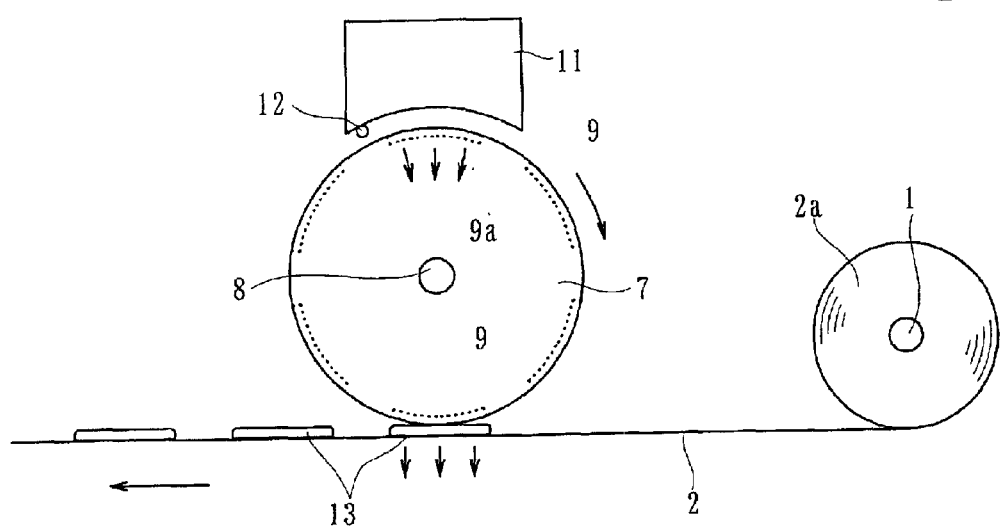
FIG. 14 is a schematic diagram showing the conventional production method of the absorbent body.

Further, in the production method shown in FIG. 3, it is also possible to combine the absorbent material layers 35A and 35B with each other to form a flat absorbent material layer as shown in FIGS. 10–12 between the cover tissues 31A and 31B, instead of laminating them to each other. In this embodiment, the absorbent material layers 35A and 35B have different absorption properties from each other, so that the resulting flat absorbent material layer has different absorption properties.

In FIG. 10, the absorbent material layer 35A is formed in a rectangular shape, while the absorbent material layer 35B is formed of four separate parts, each pair is aligned in parallel on the left and right. The absorbent material layer 35A is combined with the absorbent material layer 35B within the space provided by the four separate parts of the absorbent material layer 35B to form a flat absorbent material layer.

In FIG. 11, the absorbent material layer 35A is formed in a rectangular shape, while the absorbent material layer 35B is formed of two separate absorbent material layers in a rectangular shape lined in parallel. The absorbent material layer 35A is combined with the absorbent material layer 35B within the space provided by the two separate rectangular parts of the absorbent material layer 35B to form a flat absorbent material layer.

In FIG. 12, the absorbent material layer 35A is formed in a rectangular shape, while the absorbent material layer 35B is formed in a rectangular framework shape. The absorbent material layer 35A is combined with the absorbent material layer 35B within the space provided by the rectangular framework of the absorbent material layer 35B to form a flat absorbent material layer.

In the flat absorbent material layer shown in FIG. 10, the absorbent material layer 35B contains crushed pulp alone or a mixture of crushed pulp and SAP. The absorbent material layer 35A contains a mixture of crushed pulp and more and/or finer SAP than the absorbent material layer 35B. The particle size of the SAP in the absorbent material layer 35A is, for example, smaller than 60 mesh, preferably smaller than 100 mesh. The contents of the SAP in the absorbent material layer 35A is 20% by weight or more, preferably 30% by weight or more and more preferably, in the range of 50% to 90% by weight. In such a structure, the excrement or secretion liquid is absorbed rapidly by the absorbent material layer 35A placed at the central position and the volume of liquid retention at the absorbent material layer 35A becomes large. Therefore, the liquid spreads slowly in the direction of absorbent material layer 35B is slowed and the leakage of the liquid to the side is prevented.

In the flat absorbent material layer shown in FIG. 11, the absorbent material layer 35A contains crushed pulp alone or a mixture of crushed pulp and SAP. The absorbent material layer 35B contains a mixture of crushed pulp and more and/or finer SAP than the absorbent material layer 35A. In such an embodiment, since the liquid introduced to the absorbent material layer 35A at the central position is moved to the absorbent material layer 35B at the sides and dispersed, the liquid introduced to the absorbent material layer 35A is prevented from flowing back to the top sheet and from leaking out.

The flat absorbent material layer shown in FIG. 12 is a modification of the laminated layers composed of absorbent material layers 35 and 40 shown in FIG. 7, so that the excrement liquid introduced to the absorbent material layer 35A is absorbed by the absorbent material layer 35B formed in a rectangular framework shape.

Although the carrier tissue 33 and the cover tissue 31 are used as the cover sheets in the production methods shown in FIGS. 1 and 2, and the cover tissues 31A and 31B are used as the cover sheets in the production method shown in FIG. 3, air permeable non-woven fabrics or woven fabrics can be used as the cover sheets to produce an absorbent body (instead of using the tissues).

As described above, according to the production method of the absorbent body of the present invention, the cover sheet laid along the concavity of the pattern drum and the absorbent material layer formed on the cover sheet allow the absorbent material layer to be easily separated from the concavity of the pattern drum.

Further, according to the production method of the absorbent body of the present invention, since the particulate SAP is prevented from passing into the pattern drum through the mesh at the bottom of the concavity at the time of introducing the SAP into the absorbent material layer, the yield ratio of SAP at the production of the absorbent body can be improved. Also, it permits the introduction of very fine SAP and an increase in the SAP content in the absorbent material layer, so that the liquid retention property and the liquid absorption speed of the absorbent body can be easily improved.

Furthermore, according to the production method of the absorbent body of the present invention, the absorbent material layers can be easily laminated to each other without providing tissues between the layers. Also, it permits variation of the shapes between the absorbent material layers and to combine the absorbent material layers with each other into a single-flat layer.

While in the foregoing specification the present invention has been described in relation to preferred embodiments, and many details have been set forth for purpose of illustration, it will be apparent to those having ordinary skill in the art that the present invention is susceptible to additional embodiments and that certain of the details described herein can be varied considerably, without departing from the basic principles of the present invention.

As used herein, "comprises" and all its grammatical forms specifies the presence of stated features, integers, steps or components, but does not preclude the presence or addition of one or more other features, integers, steps, components or groups thereof.

What is claimed is:

1. A production method of an absorbent body, comprising the steps of:
supplying a first cover sheet on an outer surface of a first rotating pattern drum, said first pattern drum being provided with a first concavity formed in a predetermined shape on the outer surface thereof;
adapting the first cover sheet to the shape of the first concavity and supplying an absorbent material into the first concavity to form a first absorbent material layer adapted to the shape of the first concavity on the first cover sheet;
supplying a second cover sheet on the outer surface of a second rotating pattern drum, said second pattern drum provided with a second concavity formed in a predetermined shape on the outer surface thereof;
adapting the second cover sheet to the shape of the second concavity and supplying an absorbent material into the second concavity to form a second absorbent material layer adapted to the shape of the second concavity on the second cover sheet; and
separating the first cover sheet together with the first absorbent material layer from the outer surface of the first pattern drum and separating the second cover sheet together with the second absorbent material layer from the outer surface of the second pattern drum and superposing the first cover sheet together with the first absorbent material layer on the second cover sheet together with the second absorbent material layer to produce an absorbent body comprised of the first cover sheet, the second cover sheet and the first and second absorbent material layers interposed between the first cover sheet and the second cover sheet;
wherein each bottom of the first and second concavities is formed as a mesh, a first suction means is provided inside of the first pattern drum and a second suction means is provided inside of the second pattern drum, the suction means for sucking air through the mesh to adapt the first and second cover sheets to the shapes of the first and second concavities and for sucking air through the mesh and the first and second cover sheets to form the first and second absorbent material layers on the first and second cover sheets, and a first pressure means is provided inside of the first pattern drum and a second pressure means is provided inside of the second pattern drum, the pressure means for forcing air through the mesh to separate the first and second cover sheets together with the first and second absorbent material layers from the outer surfaces of the first and second pattern drums.

2. A production method of an absorbent body as described in claim 1, wherein the first absorbent material layer comprises absorbent fibers and optionally particulate super-absorbent polymers, and the second absorbent material layer comprises absorbent fibers and particulate super-absorbent polymers.

3. A production method of an absorbent body as described in claim 2, wherein the particle size of the super-absorbent polymers contained in the second absorbent material layer is smaller than the particle size of the super-absorbent polymers contained in the first absorbent material layer.

4. A production method of an absorbent body as described in claim 3, wherein the particle size of the super-absorbent polymers contained in the second absorbent material layer is 60 mesh or smaller.

5. A production method of an absorbent body as described in claim 2, wherein the content of the super-absorbent polymers in the second absorbent material layer is higher than the content of the super-absorbent polymers in the first absorbent material layer.

6. A production method of an absorbent body as described in claim 5, wherein the content of the super-absorbent polymers in the second absorbent material layer is 20% to 90% by weight.

7. A production method of an absorbent body as described in claim 1, wherein the first absorbent material layer and the second absorbent material layer are superposed to each other.

8. A production method of an absorbent body as described in claim 7, wherein the first absorbent material layer and the second absorbent material layer are formed in an identical shape and have different absorption properties from each other.

9. A production method of an absorbent body as described in claim 7, wherein the first absorbent material layer and the second absorbent material layer are formed in different shapes.

10. A production method of an absorbent body as described in claim 1, wherein the first absorbent material layer and the second absorbent material layer have different shapes and different absorption properties from each other and are combined adjacent to each other in a horizontal plane.

* * * * *